(12) United States Patent
Gerlach et al.

(10) Patent No.: US 6,638,933 B2
(45) Date of Patent: Oct. 28, 2003

(54) BICYCLIC IMIDAZO-3-YL-AMINE DERIVATIVES

(75) Inventors: Matthias Gerlach, Brachttal (DE); Corinna Maul, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/117,333

(22) Filed: Apr. 8, 2002

(65) Prior Publication Data

US 2003/0018032 A1 Jan. 23, 2003

Related U.S. Application Data

(62) Division of application No. PCT/EP00/09096, filed on Sep. 18, 2000.

(30) Foreign Application Priority Data

Oct. 8, 1999 (DE) .......................................... 199 48 438
Oct. 8, 1999 (DE) .......................................... 199 48 434

(51) Int. Cl.$^7$ ................... A61K 31/495; A61K 31/519; C07D 515/02; C07D 239/70; C07D 471/00
(52) U.S. Cl. ................... 514/249; 514/265; 514/300; 544/281; 544/350; 546/121
(58) Field of Search ................... 514/249, 265, 514/300; 544/281, 350; 546/121

(56) References Cited

U.S. PATENT DOCUMENTS 5,658,857 A  *  8/1997  Andree et al. ............... 504/228
6,552,037 B2 *  4/2003  Cai et al. ..................... 514/303

FOREIGN PATENT DOCUMENTS

| EP | 0068378 | 1/1983 |
| EP | 0266890 | 5/1988 |
| EP | 0518033 | 12/1992 |

OTHER PUBLICATIONS

MG Rimoli, et al., "Research on heterocyclic compounds, XXXVII. Synthesis and antiinflammatory activity of methyl-substituted imidazol[1,2-a]pyrazine derivatives" Euro J. Med. Chemistry, vol. 32, pp. 195–203.

Chemistry Abstracts, vol. 73, 1970, pp. 320–321.
Yveline Rival, et al., "Synthesis and Antibacterial Activity of Some Imidazol[1,2-a]pyrimdine Derivatives" Chem. Pharm. Bulletin, vol. 40, 1992, pp. 1170–1176.
Luigi Almurante, et al., "Derivatives of Imidazole. III. Sythesis and Pharmacological Activities of Nitriles, Amides, and Carboxylic Acid Derivatives of Imidazol[1,2-a]pyridine" J. Chem. Soc. 1968.
Hugues Bienayme, et al., "A new hetero-cyclic multi-component reaction for combinatorial synthesis of anellierten 3-aminoimidazolen" Angew. Chem. 1998.
Alain Gueiffier, et al., "Synthesis of Imidazol[1,2-a]pyridines as Antiviral Agents" J. Med. Chem., 1998.
James J. Kaminski, et al., "Antiulcer Agents. 2. Gastric Antisecretory, Cytoprotective, and Metabolic Properties of Substituted Imidazo[1,2-a]pyridines and Analogues" J. Med. Chem. 1987.
Michael H. Fisher, et al., "Imidazo[1,2-a]pyridine Anthelmintic and Antifungal Agents" Jounal of Medicinal Chemistry, vol. 15, No. 9, 1972.
Katrin Groebke, et al., "Synthesis of Imidazol[1,2-a] annulated Pyridines, Pyrazines, and Pyrimidines by a Novel Three-Component Condensation" Synlett, Jun. 1998.
Gordon B. Barlin, et al., "Imidazo[1,2-b]pyridazines: Synthesis and Interaction with Central Peripheral-Type (Mitochondrial) Benzodiazepine Receptors" J. Heterocyclic Chem. vol. 35, 1998.
Christopher Blackburn, "A Three-Component Solid-Phase Synthesis of 3-Aminoimidazo[1,2-a]azines" Tetrahedron Letters, vol. 39, 1998.
Christopher Blackburn, et al., "Parallel Synthesis of 3-Aminoimidazol[1,2-a]pyridines and pyrazines by a New Three-Component Condensation" Tetrahedron Letters, vol. 39, 1998.
Rajender S. Varma, et al., "Microwave-accelerated three-compoment condensation reaction on clay: solvent free synthesis of imidazo[1,2-a] ammulated pyridines, pyrazines and pyrimidines" Tetrahedron Letters, vol. 40, 1999.

* cited by examiner

*Primary Examiner*—D. Margaret Seaman
(74) *Attorney, Agent, or Firm*—Crowell & Moring LLP

(57) ABSTRACT

Substituted bicyclic imidazo-3-yl-amines and medicaments comprising these compounds, useful, inter alia, as analgesics.

12 Claims, No Drawings

BICYCLIC IMIDAZO-3-YL-AMINE DERIVATIVES

CROSS REFERENCE TO RELATED APPLICATIONS

The present application is a continuation of international patent application no. PCT/EP00/09096, filed Sep. 18, 2000, designating the United States of America, the entire disclosure of which is incorporated herein by reference. Priority is claimed based on Federal Republic of Germany patent application nos. 199 48 434.1, and 199 48 438.4, both filed Oct. 8, 1999.

BACKGROUND OF THE INVENTION

The present invention relates to substituted bicyclic imidazo-3-yl-amines and medicaments comprising these compounds.

Interesting pharmacological properties are known for individual compounds from the class of imidazo-3-yl-amines. Thus, certain imidazo[1,2-a]pyridines are known as active compounds which lower blood pressure (GB-B-1, 135,893), as anthelmintics and antimycotics (*J. Med. Chem.* 1972, 15, 982–985), and as antisclerotic active compounds for the treatment of inflammatory diseases (EP-A-0 068 378). EP-A-0 266 890 and *J. Med. Chem.* 1987, 30, 2031–2046 also describe an action of individual imidazopyridines against inflammatory diseases, in particular of the stomach. Further pharmacological actions described for individual representatives from the class of imidazo-3-yl-amines are antibacterial properties (*Chem. Pharm. Bull.* 1992, 40, 1170), antiviral properties (*J. Med. Chem.* 1998, 41, 5108–5112) and the action as a benzodiazepine receptor antagonist (*J. Heterocyclic Chem.* 1998, 35, 1205–1217).

In view of these interesting actions, various representatives from the class of substituted imidazo-3-yl-amines have been synthesized in the past. In particular, attempts have been made to increase the number of substituted imidazo-3-yl-amines available by combinatory synthesis processes. Thus, C. Blackburn et al. describe a three-component solid phase synthesis for the preparation of imidazo-3-yl-amines in *Tetrahedron Lett.* 1998, 39, 5469–5472 and a three-component condensation for parallel synthesis of imidazo-3-yl-amines in *Tetrahedron Lett.* 1998, 39, 3635–3638. The synthesis published by K. Groebke et al. in *Synlett* 1998, 661–663 is similar to the latter reaction. A multi-component reaction for combinatory synthesis of imidazo-3-yl-amines, with which individual imidazo-5-amines have also been prepared, is also described by H. Bienayme and K. Bouzid in *Angew. Chem.* 1998, 110 (16), 2349–2352.

However, the range of variation possible according to the prior art for the substituents on the amino nitrogen and in the 2-position of the imidazole ring was limited.

The present invention was therefore based on the object of providing further bicyclic imidazo-3-yl-amines, and medicaments comprising these compounds.

The invention therefore provides bicyclic imidazo-3-yl-amines of general formula I

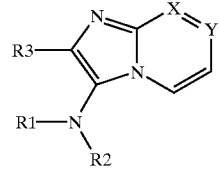

wherein

X and Y denote CH or N, with the proviso that X and Y do not simultaneously denote N, $R^1$ denotes tert-butyl, $(CH_2)_n CN$, where n=4, 5 or 6, optionally substituted phenyl, $C_4$–$C_8$-cycloalkyl, $CH_2CH_2R$ (R=4-morpholino), 1,1,3,3-tetramethylbutyl or $CH_2R^a$, wherein $R^a$ represents hydrogen, OH, $C_1$–$C_8$-alkyl (branched or unbranched), optionally substituted phenyl, CO(OR') (where R'=unbranched $C_1$–$C_4$-alkyl or branched $C_1$–$C_5$-alkyl), PO(OR')$_2$ (where R'=unbranched $C_1$–$C_4$-alkyl or branched $C_1$–$C_5$-alkyl) or Si($R^x R^y R^z$) (where $R^x$, $R^y$, and $R^z$ in each case independently of one another are $C_1$–$C_4$-alkyl (branched or unbranched), $C_4$–$C_8$-cycloalkyl or phenyl);

$R^2$ denotes hydrogen, $COR^b$, wherein $R^b$ represents $C_1$–$C_4$-alkyl (branched or unbranched) or $C_3$–$C_8$-cycloalkyl, $CH_2CH_2CO(OR^c)$, wherein $R^c$ represents $C_1$–$C_4$-alkyl (branched or unbranched), adamantyl, optionally substituted phenyl, optionally substituted 1-naphthyl or 2-naphthyl or in each case optionally substituted 2-pyridyl, 3-pyridyl, 4-pyridyl, thiazolyl or furoyl, $CH_2$-phenyl, $CH_2CH_2R^d$, wherein $R^d$ represents optionally substituted phenyl, or $CONHR^e$, wherein $R^e$ represents $C_1$–$C_8$-alkyl (branched or unbranched), $C_3$–$C_8$-cycloalkyl or optionally substituted phenyl;

$R^3$ denotes methyl, ethyl, tert-butyl, $C_3$–$C_8$-cycloalkyl, phenyl, optionally monosubstituted in the 3-, 5- or 6-position or optionally polysubstituted in the 4-position and additionally in the 2- and/or 3- and/or 5- and/or 6-position, phenoxy, optionally substituted naphthyl, optionally substituted pyrrole, optionally substituted pyridyl, optionally substituted furan, optionally substituted thiophene, optionally substituted anthracene, optionally substituted phenanthrene or optionally substituted quinoline, with the proviso that $R^3$ does not denote n-propyl, cyclohexyl, unsubstituted phenyl or phenyl monosubstituted in the 3-position with a carboxylic acid amide group if $R^1$ denotes t-butyl, n-propyl, n-butyl, 1,1,3,3-tetramethylbutyl, cyclohexyl, $CH_2CH_2R$ (R=4-morpholino), monosubstituted phenyl, 2,6-dimethylphenyl or benzyl and at the same time $R^2$ denotes hydrogen or —CO(methyl), and that $R^2$ does not denote hydrogen if at the same time $R^1$ denotes benzyl and $R^3$ denotes methyl, or at the same time $R^1$ denotes $CH_2C(O)$tert-butyl and $R^3$ denotes unsubstituted phenyl; in the form of at least one base or of at least one pharmaceutically acceptable salt.

Preferred compounds according to the invention are those in which $R^2$ denotes hydrogen; $R^1$ is selected from the group consisting of $(CH_2)_n CN$, where n=4, 5 or 6, cyclohexyl, $CH_2CO$(O-methyl), 2,6-dimethylphenyl, 1,1,3,3-tetramethylbutyl, tert-butyl or n-butyl; and $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, or 2-(trifluoromethyl)-phenyl.

Compounds which are particularly preferred according to the invention are bicyclic imidazo-3-yl-amines selected from the group consisting of

- (6-isocyano-hexyl)-(2-pyridin-2-yl-imidazo[1,2-a]pyridin-3-yl)-amine,
- (2-furan-2-yl-imidazo[1,2-a]pyridin-3-yl)-(6-isocyano-hexyl)-amine,
- (2-cyclohexyl-imidazo[1,2-a]pyrazin-3-yl)-(6-isocyano-hexyl)-amine,
- (2,6-dimethyl-phenyl)-(2-furan-2-yl-imidazo[1,2-a]pyridin-3-yl)-amine,
- (2-furan-2-yl-imidazo[1,2-a]pyrazin-3-ylamino)-acetic acid methyl ester,
- (2-cyclohexyl-imidazo[1,2-a]pyrimidin-3-ylamino)-acetic acid methyl ester,
- (2-methyl-imidazo[1,2-a]pyrazin-3-ylamino)-acetic acid methyl ester,
- (2-pyridin-4-yl-imidazo[1,2-a]pyrazin-3-yl)-(1,1,3,3-tetramethyl-butyl)-amine,
- (2-methyl-imidazo[1,2-a]pyrazin-3-yl)-(1,1,3,3-tetramethyl-butyl)-amine,
- 3-(3-tert-butylamino-imidazo[1,2-a]pyridin-2-yl)-phenol,
- butyl-[2-(2,3-dichloro-phenyl)-imidazo[1,2-a]pyrazin-3-yl]-amine,
- [(2-phenyl-imidazo[1,2-a]pyridin-3-ylamino)-methyl]-phosphonic acid diethyl ester,
- tert-butyl-(2-tert-butyl-imidazo [1,2-a]pyridin-3-yl)-amine,
- butyl-(2-o-tolyl-imidazo [1,2-a]pyrimidin-3-yl)-amine,
- (2,6-dimethyl-phenyl)-[2-(2-methoxy-phenyl)-imidazo[1,2-a]pyrazin-3-yl]-amine,
- butyl-(2-o-tolyl-imidazo[1,2-a]pyrimidin-3-yl)-amine,
- tert-butyl-(2-pyridin-3-yl-imidazo[1,2-a]pyrimidin-3-yl)-amine,
- tert-butyl-(2-methyl-imidazo[1,2-a]pyridin-3-yl)-amine,
- [2-(1H-pyrrol-2-yl)-imidazo[1,2-a]pyrimidin-3-yl]-(1,1,3,3-tetramethyl-butyl)-amine,
- cyclohexyl-(2-furan-2-yl-imidazo[1,2-a]pyridin-3-yl)-amine,
- tert-butyl-(2-pyridin-3-yl-imidazo[1,2-a]pyridin-3-yl)-amine,
- tert-butyl-(2-pyridin-2-yl-imidazo[1,2-a]pyridin-3-yl)-amine,
- tert-butyl-(2-thiophen-2-yl-imidazo[1,2-a]pyridin-3-yl)-amine,
- cyclohexyl-(2-methyl-imidazo[1,2-a]pyridin-3-yl)-amine,
- N-cyclohexyl-N-[2-(5-methyl-furan-2-yl)-imidazo[1,2-a]pyridin-3-yl]-acetamide,
- tert-butyl-[2-(5-methylsulfanyl-thiophen-2-yl)-imidazo[1,2-a]pyrimidin-3-yl]-amine,
- [2-(3-bromo-thiophen-2-yl)-imidazo[1,2-a]pyridin-3-yl]-cyclohexyl-amine, acetic acid 2-methoxy-4-[3-(1,1,3,3-tetramethyl-butylamino)-imidazo[1,2-a]pyrimidin-2-yl]-phenyl ester,
- [2-(2-chloro-4-fluoro-phenyl)-imidazo[1,2-a]pyrimidin-3-yl]-(1,1,3,3-tetramethylbutyl)-amine,
- (2-anthracen-9-yl-imidazo[1,2-a]pyrazin-3-yl)-tert-butyl-amine,
- tert-butyl-(2-naphthalen-1-yl-imidazo[1,2-a]pyridin-3-yl)-amine,
- N-cyclohexyl-N-[2-(4,5-dimethyl-furan-2-yl)-imidazo[1,2-a]pyrimidin-3-yl]-acetamide, or
- (1,1,3,3-tetramethylbutyl)-[2-(3,4,5-trimethoxy-phenyl)-imidazo[1,2-a]pyrimidin-3-yl]-amine.

If the bicyclic imidazo-3-yl-amines according to the invention contain optically active carbon atoms, the present invention also provides the enantiomers of these compounds and mixtures thereof.

The invention furthermore provides medicaments comprising as the active compound at least one bicyclic imidazo-3-yl-amine of general formula I, in which $R^1$ to $R^3$, X and Y have the abovementioned meanings, in the form of 2 base or of 2 pharmaceutically acceptable salt, preferably of hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, and/or aspartic acid, or, in particular, of hydrochloric acid.

Surprisingly, it has been found that compounds according to the invention not only are potential active compounds for the indications previously known, but also show analgesic action.

A medicament according to the invention particularly preferably comprises as an active compound at least one bicyclic imidazo-3-yl-amine selected from the group consisting of

- (6-isocyano-hexyl)-(2-pyridin-2-yl-imidazo[1,2-a]pyridin-3-yl)-amine,
- 2-furan-2-yl-imidazo[1,2-a]pyridin-3-yl)-(6-isocyano-hexyl)-amine,
- 2-cyclohexyl-imidazo[1,2-a]pyrazin-3-yl)-(6-isocyano-hexyl)-amine,
- 2,6-dimethyl-phenyl)-(2-furan-2-yl-imidazo[1,2-a]pyridin-3-yl)-amine,
- 2-furan-2-yl-imidazo[1,2-a]pyrazin-3-ylamino)-acetic acid methyl ester,
- 2-cyclohexyl-imidazo[1,2-a]pyrimidin-3-ylamino)-acetic acid methyl ester,
- 2-methyl-imidazo[1,2-a]pyrazin-3-ylamino)-acetic acid methyl ester,
- 2-pyridin-4-yl-imidazo[1,2-a]pyrazin-3-yl)-(1,1,3,3-tetramethyl-butyl)-amine,
- 2-methyl-imidazo[1,2-a]pyrazin-3-yl)-(1,1,3,3-tetramethyl-butyl)-amine,
- 3-(3-tert-butylamino-imidazo[1,2-a]pyridin-2-yl)-phenol,
- butyl-[2-(2,3-dichloro-phenyl)-imidazo[1,2-a]pyrazin-3-yl]-amine,
- [(2-phenyl-imidazo[1,2-a]pyridin-3-ylamino)-methyl]-phosphonic acid diethyl ester,
- tert-butyl-(2-tert-butyl-imidazo[1,2-a]pyridin-3-yl)-amine,
- butyl-(2-o-tolyl-imidazo[1,2-a]pyrimidin-3-yl)-amine,
- 2,6-dimethyl-phenyl)-[2-(2-methoxy-phenyl)-imidazo[1,2-a]pyrazin-3-yl]-amine,
- butyl-(2-o-tolyl-imidazo[1,2-a]pyrimidin-3-yl)-amine,
- tert-butyl-(2-pyridin-3-yl-imidazo[1,2-a]pyrimidin-3-yl)-amine, tert-butyl-(2-methyl-imidazo[1,2-a]pyridin-3-yl)-amine,
[2-(1H-pyrrol-2-yl)-imidazo[1,2-a]pyrimidin-3-yl]-(1,1,3,3-tetramethyl-butyl)-amine,
cyclohexyl-(2-furan-2-yl-imidazo[1,2-a]pyridin-3-yl)-amine,
tert-butyl-(2-pyridin-3-yl-imidazo[1,2-a]pyridin-3-yl)-amine,
tert-butyl-(2-pyridin-2-yl-imidazo[1,2-a]pyridin-3-yl)-amine,
tert-butyl-(2-thiophen-2-yl-imidazo[1,2-a]pyridin-3-yl)-amine,
cyclohexyl-(2-methyl-imidazo[1,2-a]pyridin-3-yl)-amine,
N-cyclohexyl-N-[2-(5-methyl-furan-2-yl)-imidazo[1,2-a]pyridin-3-yl]-acetamide,
tert-butyl-[2-(5-methylsulfanyl-thiophen-2-yl)-imidazo[1,2-a]pyrimidin-3-yl]-amine,
[2-(3-bromo-thiophen-2-yl)-imidazo[1,2-a]pyridin-3-yl]-cyclohexyl-amine, acetic acid 2-methoxy-4-[3-(1,1,3,3-tetramethyl-butylamino)-imidazo[1,2-a]pyrimidin-2-yl]-phenyl ester,
[2-(2-chloro-4-fluoro-phenyl)-imidazo[1,2-a]pyrimidin-3-yl]-(1,1,3,3-tetramethylbutyl)-amine,
2-anthracen-9-yl-imidazo[1,2-a]pyrazin-3-yl)-tert-butyl-amine,
tert-butyl-(2-naphthalen-1-yl-imidazo[1,2-a]pyridin-3-yl)-amine,
N-cyclohexyl-N-[2-(4,5-dimethyl-furan-2-yl)-imidazo[1,2-a]pyrimidin-3-yl]-acetamide, or
(1,1,3,3-tetramethylbutyl)-[2-(3,4,5-trimethoxy-phenyl)-imidazo[1,2-a]pyridin-3-yl]-amine, or the pharmaceutically acceptable salts of these compounds.

A particularly preferred embodiment of the present invention is a use of a bicyclic imidazo-3-yl-amine according to the invention, together with one or more auxiliary substances, for the preparation of a medicament for combating pain. Methods of treating pain in a patient in need thereof are also an embodiment of the present invention.

For the preparation of an appropriate medicament, in addition to at least one active compound according to the invention, one or more auxiliary substances, preferably at least one of carrier materials, fillers, solvents, diluents, dyestuffs and/or binders, are employed. The choice of auxiliary substances and the amounts thereof to be employed depend on whether the medicament is to be administered orally, intravenously, intraperitoneally, intradermally, intramuscularly, intranasally, buccally or locally. Formulations in the form of tablets, coated tablets, capsules, granules, drops, juices, and syrups are suitable for oral administration, and solutions, suspensions, easily reconstitutable dry formulations, and sprays are suitable for parenteral, topical and inhalatory administration. Active compounds according to the invention in a depot, in dissolved form or in a patch, optionally with the addition of agents which promote penetration through the skin, are suitable formulations for percutaneous administration. Formulation forms which can be used orally or percutaneously can release the active compounds according to the invention in a retarded manner.

The amount of active compound to be administered to the patient varies according to the weight of the patient and to the mode of administration, as well as to the indication and the severity of the disease.

The compounds according to the invention are synthesized by a procedure in which amidines with general formula II, particularly 2-aminopyridine, 2-aminopyrazine and 2-aminopyrimidine derivatives (commercially available from companies such as Acros, Avocado, Aldrich, Fluka, Lancaster, Maybridge, Merck, Sigma or TCI-Jp), are reacted with varous ketones or, preferably, aldehydes III and isonitriles IV in the presence of 20% perchloric acid in accordance with a three-component reaction. $R^1$ to $R^3$, X and Y here have the meanings given above for compounds of the formula I.

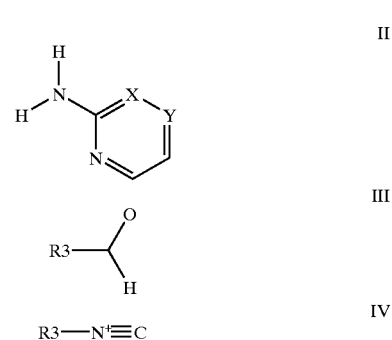

For a problem-free course of the reaction, the starting compounds are added successively in the sequence amidine II, aldehyde III, and isonitrile IV. The reactions are preferably carried out in methylene chloride at a temperature of preferably 0° C. to 40° C., in particular at a temperature of 10° C. to 20° C.

To prepare the compounds according to the invention in which $R^2$ does not denote hydrogen, the compounds Ia formed in the reaction described above, which have preferably first been dissolved in THF, are reacted, depending on the desired end product, with a compound $R^2$Hal, wherein Hal represents bromine, iodine or, particularly, chlorine, for example an optionally substituted alkyl, aryl or acid chloride, or an optionally substituted isocyanate $R^e$NCO in the presence of a morpholine resin (e.g., polystyrene-morpholine from Argonaut) in methylene chloride in the course of 2 to 24 hours at temperatures between 10° C. and 40° C. in accordance with the following equation:

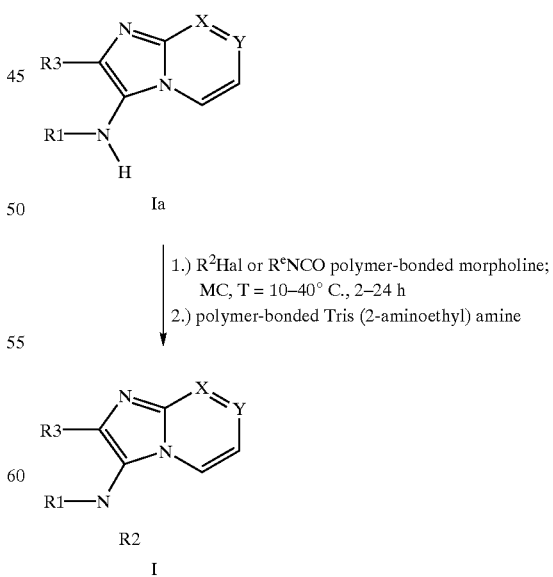

The excess reagents are then removed from the reaction mixtures by filtration over a layer with polymer-bonded tris(2-aminoethyl)amine (manufacturer: Novabiochem) or 3-(3-mercaptophenyl)propanamidomethylpolystyrene and the filtrate is concentrated, for example, in a vacuum centrifuge. The entire process can also easily be carried out in an automated synthesis unit.

The compounds of the formula I can be converted into their salts in a known manner with physiologically tolerated acids, preferably hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, and/or aspartic acid, and particularly hydrochloric acid. The salt formation is preferably carried out in a solvent, preferably diethyl ether, diisopropyl ether, acetic acid alkyl esters, acetone, or 2-butanone, or in a mixture of these solvents. Alternatively, trimethylsilane in aqueous solution is also suitable for preparation of the hydrochlorides.

EXAMPLES

The following examples are intended to illustrate the invention without limiting it thereto.

General Instructions 1 (Automatic Synthesis)

The synthesis of the compounds was carried out in an automatic unit from Zymark in accordance with the following general synthesis instructions:

A round-bottomed tube of glass (diameter 16 mm, length 125 mm) with a thread was provided manually with a stirrer and closed with a screw-cap with a septum on the capper station. The tube was placed by robot 1 in the reactor block temperature-controlled at 15° C. Robot 2 pipetted in the following reagents in succession:

1.) 1 ml of a 0.1 M amidine solution+20% $HClO_4$ in methylene chloride
2.) 0.5 ml of a 0.3 M aldehyde solution in methylene chloride
3.) 0.575 ml of a 0.2 M isonitrile solution in methylene chloride The reaction mixture was stirred at 15° C. in one of the stirring blocks for 660 min. Thereafter, the reaction solution was filtered at the filtration station. The tube was rinsed here twice with in each case 1 ml methylene chloride and 200 μl water.

The rack with the tubes was then placed manually on the working-up unit. On this, 3 ml of a 10% NaCl solution and 1.5 ml methylene chloride were added to the reaction mixture on a vortexer. The components were mixed thoroughly in the spin reactor for ten minutes and a clear phase boundary was formed by slowly decreasing the rotational movement. This phase boundary was detected optically and the organic phase was pipetted off. In the next step, 1.5 ml methylene chloride were again added to the reaction mixture. The solution was shaken and centrifuged and the organic phase was pipetted off. The combined organic phases were dried over 2.4 g $MgSO_4$ (granulated). The solvent was removed in a vacuum centrifuge.

General Instructions 2 (Manual Synthesis)

(Equivalents denote molar equivalents, based on the isonitrile employed):

1.15 equivalents of the heterocyclic amine were first suspended or dissolved in methylene chloride (2 ml per mmol of isonitrile employed) in a suitable reaction vessel. 1.5 equivalents of aldehyde, one equivalent of isonitrile and finally aqueous perchloric acid solution (20 m %; 0.098 ml per mmol of isonitrile employed) were added to this in succession and the mixture was stirred at room temperature for twenty hours.

For working up, saturated sodium chloride solution (approximately 5 ml per mmol of isonitrile employed) and methylene chloride (approximately 4 ml per mmol of isonitrile employed) were added, the phases were separated, and the organic phase was extracted twice more with methylene chloride (in each case approx. 2 ml per mmol of isonitrile was employed). The combined organic phases were washed in succession with buffer solution (pH 10; approximately 2 ml per mmol of isonitrile employed) and saturated sodium chloride solution (approximately 2 ml per mmol of isonitrile employed), dried over sodium sulfate and filtered. The filtrate was concentrated on a rotary evaporator in vacuo and the residue was freed from solvent residues under an oil pump vacuum.

The chemicals and solvents employed were obtained commercially. Each substance was analyzed by ESI-MS and/or NMR.

General Instructions 3 (Reaction with Acetyl Chloride)

The product obtained in accordance with general instructions 1 was dissolved in methylene chloride, 4 molar equivalents of acetyl chloride were added, and the mixture was stirred at 18° C. for four hours. The excess acetyl chloride and the solvent were removed in vacuo at 40–60° C. Each substance was analyzed by ESI-MS.

Example 1

(6-Isocyano-hexyl)-(2-pyridin-2-yl-imidazo[1,2-a]pyridin-3-yl)-amine (1)

Compound (1) was prepared in accordance with general instructions 1 from 1.0 ml 2-aminopyridine solution (0.1 M, MC), 0.575 ml 1,6-diisocyanohexane solution (0.2 M, MC), 0.500 ml pyridine-2-carbaldehyde solution (0.3 M, MC), and 10 μl perchloric acid (w=20%).

Calculated mass 321.43; found mass M–H=320.4 (ESI-MS)

Example 2

(2-Furan-2-yl-imidazo[1,2-a]pyridin-3-yl)-(6-isocyano-hexyl)-amine (2)

Compound (2) was prepared in accordance with general instructions 1 from 1.0 ml 2-aminopyridine solution (0.1 M, MC), 0.575 ml 1,6-diisocyanohexane solution (0.2 M, MC), 0.500 ml furfural solution (0.3 M, MC), and 10 μl perchloric acid (w=20%).

Calculated mass 310.40; found mass M–H=309.4 (ESI-MS)

Example 3

(2-Cyclohexyl-imidazo[1,2-a]pyrazin-3-yl)-(6-isocyano-hexyl)-amine (3)

Compound (3) was prepared in accordance with general instructions 1 from 1.0 ml aminopyrazine solution (0.1 M, MC), 0.575 ml 1,6-diisocyanohexane solution (0.2 M, MC), 0.500 ml cyclohexanecarbaldehyde solution (0.3 M, MC), and 10 μl perchloric acid (w=20%).

Calculated mass 327.48; found mass M–H=326.5 (ESI-MS)

Example 4

(2,6-Dimethyl-phenyl)-2-furan-2-yl-imidazo[1,2-a]pyridin-3-yl)-amine-(4)

Compound (4) was prepared in accordance with general instructions 1 from 1.0 ml 2-aminopyridine solution (0.1 M, MC), 0.575 ml 2,6-dimethylphenylisonitrile solution (0.2 M, MC), 0.500 ml furfural solution (0.3 M, MC), and 10 µl perchloric acid (w=20%).

Calculated mass 303.37; found mass=304.4 (ESI-MS)

Example 5

(2-Furan-2-yl-imidazo[1,2-a]pyrazin-3-ylamino)-acetic acid methyl ester (5)

Compound (5) was prepared in accordance with general instructions 1 from 1.0 ml aminopyrazine solution (0.1 M, MC), 0.575 ml methyl isocyanoacetate solution (0.2 M, MC), 0.500 ml furfural solution (0.3 M, MC), and 10 µl perchloric acid (w=20%).

Calculated mass 272.27; found mass=273.4 (ESI-MS)

Example 6

(2-Cyclohexyl-imidazo[1,2-a]pyrimidin-3-ylamino)-acetic acid methyl ester (6)

Compound (6) was prepared in accordance with general instructions 1 from 1.0 ml 2-aminopyrimidine solution (0.1 M, MC), 0.575 ml methyl isocyanoacetate solution (0.2 M, MC); 0.500 ml cyclohexylcarbaldehyde solution (0.3 M, MC), and 10 µl perchloric acid (w=20%).

Calculated mass 288.35; found mass=289.4 (ESI-MS)

Example 7

(2-Methyl-imidazo[1,2-a]pyrazin-3-ylamino)-acetic acid methyl ester

Compound (7) was prepared in accordance with general instructions 1 from 1.0 ml aminopyrazine solution (0.1 M, MC), 0.575 ml methyl isocyanoacetate solution (0.2 M, MC), 0.500 ml acetaldehyde solution (0.3 M, MC), and 10 µl perchloric acid (w=20%).

Calculated mass 220.23; found mass=221.3 (ESI-MS

Example 8

(2-Pyridin-4-yl-imidazo[1,2-a]pyrazin-3-yl)-(1,1,3,3-tetramethyl-butyl)-amine (8)

Compound (8) was prepared in accordance with general instructions 1 from 1.0 ml aminopyrazine solution (0.1 M, MC), 0.575 ml 1,1,3,3-tetramethylbutyl isocyanide (0.2 M, MC), 0.500 ml pyridine-4-carbaldehyde solution (0.3 M, MC), and 10 µl perchloric acid (w=20%).

Calculated mass 323.44; found mass=324.4 (ESI-MS)

Example 9

(2-Methyl-imidazo[1,2-a]pyrazin-3-yl)-(1,1,3,3-tetramethyl-butyl)-amine

Compound (9) was prepared in accordance with general instructions 1 from 1.0 ml aminopyrazine solution (0.1 M, MC), 0.575 ml 1,1,3,3-tetramethylbutyl isocyanide (0.2 M, MC), 0.500 ml acetaldehyde solution (0.3 M, MC), and 10 µl perchloric acid (w=20%).

Calculated mass 260.39; found mass=261.4 (ESI-MS)

Example 10

(3-(3-tert-Butylamino-imidazo[1,2-a]pyridin-2-yl)-phenol (10)

Compound (10) was prepared in accordance with general instructions 1 from 1.0 ml 2-aminopyridine solution (0.1 M, MC), 0.575 ml tert-butylisonitrile solution (0.2 M, MC), 0.500 ml 3-hydroxybenzaldehyde solution (0.3 M, MC) and 10 µl perchloric acid (w=20%).

Calculated mass 281.36; found mass=282.3 (ESI-MS)

Example 11

Butyl-[2-(2,3-dichloro-phenyl)-imidazo[1,2-a]pyrazin-3-yl]-amine (11)

Compound (11) was prepared in accordance with general instructions 1 from 1.0 ml aminopyrazine solution (0.1 M, MC), 0.575 ml n-butylisonitrile solution (0.2 M, MC), 0.500 ml 2,3-dichlorobenzaldehyde solution (0.3 M, MC), and 10 µl perchloric acid (w=20%).

Calculated mass 335.24; found mass=335.4 (ESI-MS)

Example 12

[(2-Phenyl-imidazo[1,2-a]pyridin-3-ylamino)-methyl]-phosphonic acid diethyl ester (12)

Compound (12) was prepared in accordance with general instructions 2 from 2-aminopyridine, diethyl isocyanomethyl phosphate, benzaldehyde, and perchloric acid (w=20%). The structure was confirmed by NMR spectroscopy.

Example 13 tert-Butyl-(2-tert-butyl-imidazo[1,2-a]pyridin-3-yl)-amine (13)

Compound (13) was prepared in accordance with general instructions 2 from 2-aminopyridine, tert-butylisonitrile, pivaldehyde, and perchloric acid.

The structure was confirmed by NMR spectroscopy.

Example 14

Butyl-(2-o-tolyl-imidazo[1,2-a]pyrimidin-3-yl)-amine (14)

Compound (14) was prepared in accordance with the general instructions from 1.0 ml 2-aminopyrimidine solution (0.1 M, MC), 0.575 ml n-butylisonitrile solution (0.2 M, MC), 0.500 ml 2-methylbenzaldehyde solution (0.3 M, MC), and 10 µl perchloric acid (w=20%).

Calculated mass 280.38; found mass 281.3 (ESI-MS)

Example 15

(2,6-Dimethyl-phenyl)-[2-(2-methoxy-phenyl)-imidazo[1,2-a]pyrazin-3-yl]-amine (15)

Compound (15) was prepared in accordance with general instructions 1 from 1.0 ml aminopyrazine solution (0.1 M, MC), 0.575 ml 2,6-dimethylphenyl isocyanide solution (0.2 M, MC), 0.500 ml 2-methoxybenzaldehyde solution (0.3 M, MC), and 10 µl perchloric acid (w=20%).

Calculated mass 344.42; found mass=345.4 (ESI-MS)

Example 16

Butyl-(2-o-tolyl-imidazo[1,2-a]pyrimidin-3-yl)-amine (16)

Compound (16) was prepared in accordance with general instructions 1 from 1.0 ml 2-aminopyrimidine solution (0.1 M, MC), 0.575 ml n-butylisonitrile solution (0.2 M, MC), 0.500 ml 2-methylbenzaldehyde solution (0.3 M, MC), and 10 µl perchloric acid (w=20%).

Calculated mass 280.38; found mass=281.3 (ESI-MS)

Example 17 tert-Butyl-(2-pyridin-3-yl-imidazo[1,2-a]pyrimidin-3-yl)-amine (17)

Compound (17) was prepared in accordance with general instructions 1 from 1.0 ml 2-aminopyrimidine solution (0.1

M, MC), 0.575 ml tert-butylisonitrile solution (0.2 M, MC), 0.500 ml pyridine-3-carbaldehyde solution (0.3 M, MC), and 10 μl perchloric acid (w=20%).

Calculated mass 267.34; found mass=268.3 (ESI-MS)

Example 18 tert-Butyl-(2-methyl-imidazo[1,2-a]pyridin-3-yl)-amine (18)

Compound (18) was prepared in accordance with general instructions 1 from 1.0 ml 2-aminopyridine solution (0.1 M, MC), 0.575 ml tert-butylisonitrile solution (0.2 M, MC), 0.500 ml acetaldehyde solution (0.3 M, MC), and 10 μl perchloric acid (w=20%).

Calculated mass 203.29; found mass=204.3 (ESI-MS)

Example 19

[2-(1H-Pyrrol-2-yl)-imidazo[1,2-a]pyrimidin-3-yl]-(1,1,3,3-tetramethyl-butyl)-amine (19)

Compound (19) was prepared in accordance with general instructions 1 from 1.0 ml 2-aminopyrimidine solution (0.1 M, MC), 0.575 ml 1,1,3,3-tetramethylbutyl isocyanide solution (0.2 M, MC), 0.500 ml pyrrole-2-carbaldehyde solution (0.3 M, MC), and 10 μl perchloric acid (w=20%).

Calculated mass 311.43; found mass=312.4 (ESI-MS)

Example 20

Cyclohexyl-(2-furan-2-yl-imidazo[1,2-a]pyridin-3-yl)-amine (20)

Compound (20) was prepared in accordance with general instructions 2 from 2-aminopyridine, cyclohexylisonitrile, furfural, and perchloric acid.

The structure was confirmed by NMR spectroscopy.

Example 21 tert-Butyl-(2-pyridin-3-yl-imidazo[1,2-a]pyridin-3-yl)-amine (21)

Compound (21) was prepared in accordance with general instructions 2 from 2-aminopyridine, tert-butylisonitrile, nicotinaldehyde, and perchloric acid.

The structure was confirmed by NMR spectroscopy.

Example 22 tert-Butyl-(2-pyridin-2-yl-imidazo[1,2-a]pyridin-3-yl)-amine (22)

Compound (22) was prepared in accordance with general instructions 2 from 2-aminopyridine, tert-butylisonitrile, 2-pyridylcarbaldehyde, and perchloric acid.

The structure was confirmed by NMR spectroscopy.

Example 23 tert-Butyl-(2-thiophen-2-yl-imidazo[1,2-a]pyridin-3-yl)-amine (23)

Compound (23) was prepared in accordance with general instructions 2 from 2-aminopyridine, tert-butylisonitrile, thiophene-2-carbaldehyde, and perchloric acid.

The structure was confirmed by NMR spectroscopy.

Example 24

Cyclohexyl-(2-methyl-imidazo[1,2-a]pyridin-3-yl)-amine (24)

Compound (24) was prepared in accordance with general instructions 2 from 2-aminopyridine, cyclohexylisonitrile, acetaldehyde, and perchloric acid The structure was confirmed by NMR spectroscopy. .

Example 25

N-Cyclohexyl-N-[2-(5-methyl-furan-2-yl)-imidazo[1,2-a]pyridin-3-yl]acetamide (25)

Compound (25) was prepared by reaction of the product obtained in accordance with general instructions 1 from 1.0 ml 2-aminopyridine solution (0.1 M, MC), 0.575 ml cyclohexyl isocyanide solution (0.2 M, MC), 0.500 ml 5-methylfurfural solution (0.3 M, MC), and 10 μl perchloric acid (w=20%) with acetyl chloride in accordance with general instructions 3.

Calculated mass 337.4; found mass 338.5; M-acetyl 296.5 (ESI-MS)

Example 26 tert-Butyl-[2-(5-methylsulfanyl-thiophen-2-yl)-imidazo[1,2-a]pyrimidin-3-yl]-amine (26)

Compound (26) was prepared in accordance with general instructions 1 from 1.0 ml 2-aminopyrimidine solution (0.1 M, MC), 0.575 ml tert-butylisonitrile isocyanide solution (0.2 M, MC), 0.500 ml 5-methylsulfanyl-thiophene-2-carbaldehyde solution (0.3 M, MC), and 10 μl perchloric acid (w=20%). Calculated mass 318.5; found mass 319.2 (ESI-MS)

Example 27

[2-(3-Bromo-thiophen-2-yl)-imidazo[1,2-a]pyridin-3-yl]-cyclohexyl-amine (27)

Compound (27) was prepared in accordance with general instructions 1 from 1.0 ml 2-aminopyridine solution (0.1 M, MC), 0.575 ml cyclohexyl isocyanide solution (0.2 M, MC), 0.500 ml 3-bromothiophene-2-carbaldehyde solution (0.3 M, MC), and 10 μl perchloric acid (w=20%). Calculated mass 376.3; found mass 376.4/378.3 (ESI-MS)

Example 28

Acetic acid 2-methoxy-4-[3-(1,1,3,3-tetramethyl-butylamino)-imidazo[1,2-a]pyrimidin-2-yl]-phenyl ester (28)

Compound (28) was prepared in accordance with general instructions 1 from 1.0 ml 2-aminopyrimidine solution (0.1 M, MC), 0.575 ml 1,1,3,3-tetramethylbutyl isocyanide solution (0.2 M, MC), 0.500 ml acetic acid 4-formyl-2-methoxy-phenyl ester solution (0.3 M, MC), and 10 μl perchloric acid (w=20%). Calculated mass 410.5; found mass 411.3 (ESI-MS)

Example 29

[2-(2-Chloro-4-fluoro-phenyl)-imidazo[1,2-a]pyrimidin-3-yl]-(1,1,3,3-tetramethylbutyl)-amine (29)

Compound (29) was prepared in accordance with general instructions 1 from 1.0 ml 2-aminopyrimidine solution (0.1 M, MC), 0.575 ml 1,1,3,3-tetramethylbutyl isocyanide solution (0.2 M, MC), 0.500 ml 2-chloro-4-fluorobenzaldehyde solution (0.3 M, MC), and 10 μl perchloric acid (w=20%). Calculated mass 374.9; found mass 375.3 (ESI-MS)

Example 30

(2-Anthracen-9-yl-imidazo[1,2-a]pyrazin-3-yl)-tert-butyl-amine (30)

Compound (30) was prepared in accordance with general instructions 1 from 1.0 ml 2-aminopyrazine solution (0.1 M, MC), 0.575 ml tert-butyl isocyanide solution (0.2 M, MC), 0.500 ml anthracene-9-carbaldehyde solution (0.3 M, MC), and 10 µl perchloric acid (w=20%). Calculated mass 366.5; found mass 367.3 (ESI-MS).

Example 31 tert-Butyl-(2-naphthalen-1-yl-imidazo[1,2-a]pyridin-3-yl)-amine (31)

Compound (31) was prepared in accordance with general instructions 1 from 1.0 ml 2-aminopyridine solution (0.1 M, MC), 0.575 ml tert-butyl isocyanide solution (0.2 M, MC), 0.500 ml naphthalene-1-carbaldehyde solution (0.3 M, MC), and 10 µl perchloric acid (w=20%). Calculated mass 315.4; found mass 316.3 (ESI-MS)

Example 32

N-Cyclohexyl-N-[2-(4,5-dimethyl-furan-2-yl)-imidazo[1,2-a]pyrimidin-3-yl]-acetamide (32)

Compound (32) was prepared by reaction of the product obtained in accordance with general instructions 1 from 1.0 ml 2-aminopyrimidine solution (0.1 M, MC), 0.575 ml cyclohexyl isocyanide solution (0.2 M, MC), 0.500 ml 4,5-dimethylfurfural solution (0.3 M, MC), and 10 µl perchloric acid (w=20%) with acetyl chloride in accordance with general instructions 3. Calculated mass 352.4; found mass 353.4 (ESI-MS)

Example 33

(1,1,3,3-Tetramethylbutyl)-[2-(3,4,5-trimethoxy-phenyl)-imidazo[1,2-a]pyridin-3-yl]-amine (33)

Compound (33) was prepared in accordance with general instructions 1 from 1.0 ml 2-aminopyridine solution (0.1 M, MC), 0.575 ml 1,1,3,3-tetramethylbutyl isocyanide solution (0.2 M, MC), 0.500 ml 3,4,5-trimethoxybenzaldehyde solution (0.3 M, MC), and 10 Al perchloric acid (w=20%).

Calculated mass 411.5; found mass 412.3 (ESI-MS)

Analgesia Test in the Writhing Test in Mice

The analgesic activity was investigated in the phenylquinone-induced writhing in mice (modified according to I. C. Hendershot, J. Forsaith, *J. Pharmacol. Exp. Ther.* 125, 237–240 (1959)). Male NMRI mice weighing 25–30 g were used. Groups of 10 animals per substance dose received 0.3 ml/mouse of a 0.02% aqueous solution of phenylquinone (phenylbenzoquinone, Sigma, Deisenhofen; solution prepared with the addition of 5% ethanol and storage in a water-bath at 45° C.) administered intraperitoneally ten minutes after intravenous or subcutaneous administration of the test substances. The animals were placed individually in observation cages. The number of pain-induced extension movements (so-called writhing reactions=straightening of the body with stretching out of the hind extremities) 5–20 minutes after administration of the phenylquinone was counted by means of a push-button counter. Animals which receive only physiological saline solution were also run as a control. The substances were tested in the standard dosage of 10 mg/kg intravenously or 21.5 mg/kg subcutaneously. The percentage inhibition (% inhibition) of the writhing reaction by a substance was calculated in accordance with the following equation:

$$\% \text{ inhibition} = 100 - \frac{\text{Writhing reactions of the treated animals}}{\text{Writhing reactions of the control animals}} * 100$$

The compounds according to the invention investigated showed an analgesic action. The results are summarized in the following table.

TABLE

| | Analgesia test in the writhing test in mice | |
|---|---|---|
| Example | % inhibition of the writhing reaction at 21.5 mg/kg subcutaneously | % inhibition of the writhing reaction at 10 mg/kg intravenously |
| 12 | | 90 |
| 13 | | 86 at 2.15 mg/kg |
| 20 | | 43 |
| 21 | 80 | |
| 22 | | 53 |
| 23 | | 62 |
| 24 | | 56 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

We claim:

1. A compound of formula I:

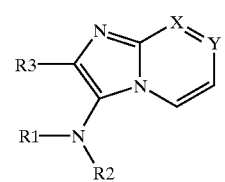

wherein

X and Y each separately denote CH or N, with the proviso that X and Y do not simultaneously denote N;

$R^1$ denotes tert-butyl, $(CH_2)_nCN$, where n=4, 5 or 6, optionally substituted phenyl, $C_4$–$C_8$-cycloalkyl, $CH_2CH_2R$ (R=4-morpholino), 1,1,3,3-tetramethylbutyl, or $CH_2R^a$ wherein $R^a$ represents hydrogen, OH, branched or unbranched $C_1$–$C_8$-alkyl, optionally substituted phenyl, CO(OR') wherein R'=unbranched $C_1$–$C_4$-alkyl or branched $C_1$–$C_5$-alkyl, $PO(OR')_2$ wherein R'=unbranched $C_1$–$C_4$-alkyl or branched $C_1$–$C_5$-alkyl, or $Si(R^xR^yR^z)$ wherein $R^x$, $R^y$ and $R^z$ are each selected independently of one another from branched or unbranched $C_1$–$C_4$-alkyl, $C_4$–$C_8$-cycloalkyl, and phenyl;

$R^2$ denotes hydrogen, $COR^b$, wherein $R^b$ represents branched or unbranched $C_1$–$C_4$-alkyl or $C_3$–$C_8$-cycloalkyl, $CH_2CH_2CO(OR^c)$, wherein $R^c$ represents branched or unbranched $C_1$–$C_4$-alkyl, adamantyl, optionally substituted phenyl, optionally substituted 1-naphthyl, optionally substituted 2-naphthyl, optionally substituted 2-pyridyl, optionally substituted 3-pyridyl, optionally substituted 4-pyridyl, optionally substituted thiazolyl, optionally substituted furoyl, benzyl, $CH_2CH_2R^d$ wherein $R^d$ represents optionally substituted phenyl, or $CONHR^e$ wherein $R^e$ represents branched or unbranched $C_1$–$C_8$-alkyl, $C_3$–$C_8$-cycloalkyl, or optionally substituted phenyl;

$R^3$ denotes methyl, ethyl, tert-butyl, $C_3$–$C_8$-cycloalkyl, phenyl wherein said phenyl is optionally monosubstituted in the 3-, 5- or 6-position, or wherein said phenyl is optionally at least di-substituted in the 4-position and additionally in at least one of the 2-, 3-, 5-, and 6-positions, phenoxy, optionally substituted naphthyl, optionally substituted pyrrole, optionally substituted pyridyl, optionally substituted furan, optionally substituted thiophene, optionally substituted anthracene, optionally substituted phenanthrene, or optionally substituted quinoline;

wherein any radical denoted optionally substituted is unsubstituted, or is at least mono-substituted with a moiety selected from the group consisting of OH, nitro, amino, amido, cyano, CO—$C_1$–$C_8$-alkyl, CO—O—$C_1$–$C_8$-alkyl, $CO_2H$, O—$C_1$–$C_8$-alkyl, O-heteroalkyl, halogen, branched or unbranched $C_1$–$C_8$-alkyl, $C_3$–$C_8$-cycloalkyl, $C_3$–$C_8$-heterocyclyl, unsubstituted or substituted phenyl, unsubstituted or substituted heteroaryl, wherein any ring, aromatic or unsaturated, may be fused to other rings, any moeity optionally has one or more double or triple bonds, and any alkyl or aromatic moiety is unsubstituted or is substituted with a moiety selected from this group;

with the proviso that if $R^1$ is tert-butyl, n-propyl, n-butyl, 1,1,3,3-tetramethylbutyl, cyclohexyl, $CH_2CH_2R$ wherein R=4-morpholino, monosubstituted phenyl, 2,6-dimethylphenyl or benzyl, and $R^2$ is hydrogen or —CO(methyl), $R^3$ is not n-propyl, cyclohexyl, unsubstituted phenyl, or phenyl monosubstituted in the 3-position with a carboxylic acid amide group;

with the further proviso that if $R^1$ denotes benzyl, and $R^3$ is methyl, $R^2$ is not hydrogen;

with the further proviso that if $R^1$ is $CH_2C(O)$tert-butyl, and $R^3$ is unsubstituted phenyl, $R^2$ is not hydrogen;

or a pharmaceutically acceptable salt thereof.

2. A compound according to claim 1, wherein $R^2$ denotes hydrogen;

$R^1$ is selected from the group consisting of $(CH_2)_nCN$, where n=4, 5 or 6, cyclohexyl, $CH_2CO$(O-methyl), 2,6-dimethylphenyl, 1,1,3,3-tetramethylbutyl, tert-butyl, and n-butyl; and $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)phenyl.

3. A compound according to claim 1, wherein said compound is selected from the group consisting of (6-isocyano-hexyl)-(2-pyridin-2-yl-imidazo[1,2-a]pyridin-3-yl)-amine, (2-furan-2-yl-imidazo[1,2-a]pyridin-3-yl)-(6-isocyano-hexyl)-amine, (2-cyclohexyl-imidazo[1,2-a]pyrazin-3-yl)-(6-isocyano-hexyl)-amine, (2,6-dimethyl-phenyl)-(2-furan-2-yl-imidazo[1,2-a]pyridin-3-yl)-amine, (2-furan-2-yl-imidazo[1,2-a]pyrazin-3-ylamino)-acetic acid methyl ester, (2-cyclohexyl-imidazo[1,2-a]pyrimidin-3-ylamino)-acetic acid methyl ester, (2-methyl-imidazo[1,2-a]pyrazin-3-ylamino)-acetic acid methyl ester, (2-pyridin-4-yl-imidazo[1,2-a]pyrazin-3-yl)-(1,1,3,3-tetramethyl-butyl)-amine, (2-methyl-imidazo[1,2-a]pyrazin-3-yl)-(1,1,3,3-tetramethyl-butyl)-amine, 3-(3-tert-butylamino-imidazo[1,2-a]pyridin-2-yl)-phenol, butyl-[2-(2,3-dichloro-phenyl)-imidazo[1,2-a]pyrazin-3-yl]-amine,

[(2-phenyl-imidazo[1,2-a]pyridin-3-ylamino)-methyl]-phosphonic acid diethyl ester, tert-butyl-(2-tert-butyl-imidazo[1,2-a]pyridin-3-yl)-amine, butyl-(2-o-tolyl-imidazo[1,2-a]pyrimidin-3-yl)-amine, (2,6-dimethyl-phenyl)-[2-(2-methoxy-phenyl)-imidazo[1,2-a]pyrazin-3-yl]-amine, butyl-(2-o-tolyl-imidazo[1,2-a]pyrimidin-3-yl)-amine, tert-butyl-(2-pyridin-3-yl-imidazo[1,2-a]pyrimidin-3-yl)-amine, tert-butyl-(2-methyl-imidazo[1,2-a]pyridin-3-yl)-amine,

[2-(1H-pyrrol-2-yl)-imidazo[1,2-a]pyrimidin-3-yl]-(1,1,3,3-tetramethyl-butyl)-amine, cyclohexyl-(2-furan-2-yl-imidazo[1,2-a]pyridin-3-yl)-amine, tert-butyl-(2-pyridin-3-yl-imidazo[1,2-a]pyridin-3-yl)-amine, tert-butyl-(2-pyridin-2-yl-imidazo[1,2-a]pyridin-3-yl)-amine, tert-butyl-(2-thiophen-2-yl-imidazo[1,2-a]pyridin-3-yl)-amine, cyclohexyl-(2-methyl-imidazo[1,2-a]pyridin-3-yl)-amine, N-cyclohexyl-N-[2-(5-methyl-furan-2-yl)-imidazo[1,2-a]pyridin-3-yl]-acetamide, tert-butyl-[2-(5-methylsulfanyl-thiophen-2-yl)-imidazo[1,2-a]pyrimidin-3-yl]-amine,

[2-(3-bromo-thiophen-2-yl)-imidazo[1,2-a]pyridin-3-yl]-cyclohexyl-amine, acetic acid 2-methoxy-4-[3-(1,1,3,3-tetramethyl-butylamino)-imidazo[1,2-a]pyrimidin-2-yl]-phenyl ester,

[2-(2-chloro-4-fluoro-phenyl)-imidazo[1,2-a]pyrimidin-3-yl]-(1,1,3,3-tetramethylbutyl)-amine, (2-anthracen-9-yl-imidazo[1,2-a]pyrazin-3-yl)-tert-butyl-amine, tert-butyl-(2-naphthalen-1-yl-imidazo[1,2-a]pyridin-3-yl)-amine, N-cyclohexyl-N-[2-(4,5-dimethyl-furan-2-yl)-imidazo[1,2-a]pyrimidin-3-yl]-acetamide, and (1,1,3,3-tetramethyl-butyl)-[2-(3,4,5-trimethoxy-phenyl)-imidazo[1,2-a]pyridin-3-yl]-amine.

4. A pharmaceutical composition, comprising at least one compound according to claim 1, and at least one auxiliary substance.

5. A pharmaceutical composition according to claim 4, wherein said at least one compound is selected from the group consisting of
(6-isocyano-hexyl)-(2-pyridin-2-yl-imidazo[1,2-a]pyridin-3-yl)-amine,
(2-furan-2-yl-imidazo[1,2-a]pyridin-3-yl)-(6-isocyano-hexyl)-amine,
(2-cyclohexyl-imidazo[1,2-a]pyrazin-3-yl)-(6-isocyano-hexyl)-amine,
(2,6-dimethyl-phenyl)-(2-furan-2-yl-imidazo[1,2-a]pyridin-3-yl)-amine,
(2-furan-2-yl-imidazo[1,2-a]pyrazin-3-ylamino)-acetic acid methyl ester,
(2-cyclohexyl-imidazo[1,2-a]pyrimidin-3-ylamino)-acetic acid methyl ester,
(2-methyl-imidazo[1,2-a]pyrazin-3-ylamino)-acetic acid methyl ester,
(2-pyridin-4-yl-imidazo[1,2-a]pyrazin-3-yl)-(1,1,3,3-tetramethyl-butyl)-amine,
(2-methyl-imidazo[1,2-a]pyrazin-3-yl)-(1,1,3,3-tetramethyl-butyl)-amine,
3-(3-tert-butylamino-imidazo[1,2-a]pyridin-2-yl)-phenol,
butyl-[2-(2,3-dichloro-phenyl)-imidazo[1,2-a]pyrazin-3-yl]-amine,
[(2-phenyl-imidazo[1,2-a]pyridin-3-ylamino)-methyl]-phosphonic acid diethyl ester,
tert-butyl-(2-tert-butyl-imidazo[1,2-a]pyridin-3-yl)-amine,
butyl-(2-o-tolyl-imidazo[1,2-a]pyrimidin-3-yl)-amine,
(2,6-dimethyl-phenyl)-[2-(2-methoxy-phenyl)-imidazo[1,2-a]pyrazin-3-yl]-amine,
butyl-(2-o-tolyl-imidazo[1,2-a]pyrimidin-3-yl)-amine,
tert-butyl-(2-pyridin-3-yl-imidazo[1,2-a]pyrimidin-3-yl)-amine,
tert-butyl-(2-methyl-imidazo[1,2-a]pyridin-3-yl)-amine,
[2-(1H-pyrrol-2-yl)-imidazo[1,2-a]pyrimidin-3-yl]-(1,1,3,3-tetramethyl-butyl)-amine,
cyclohexyl-(2-furan-2-yl-imidazo[1,2-a]pyridin-3-yl)-amine,
tert-butyl-(2-pyridin-3-yl-imidazo[1,2-a]pyridin-3-yl)-amine,
tert-butyl-(2-pyridin-2-yl-imidazo[1,2-a]pyridin-3-yl)-amine,
tert-butyl-(2-thiophen-2-yl-imidazo[1,2-a]pyridin-3-yl)-amine,
cyclohexyl-(2-methyl-imidazo[1,2-a]pyridin-3-yl)-amine,
N-cyclohexyl-N-[2-(5-methyl-furan-2-yl)-imidazo[1,2-a]pyridin-3-yl]-acetamide,
tert-butyl-[2-(5-methylsulfanyl-thiophen-2-yl)-imidazo[1,2-a]pyrimidin-3-yl]-amine,
[2-(3-bromo-thiophen-2-yl)-imidazo[1,2-a]pyridin-3-yl]-cyclohexyl-amine, acetic acid 2-methoxy-4-[3-(1,1,3,3-tetramethyl-butylamino)-imidazo[1,2-a]pyrimidin-2-yl]-phenyl ester,
[2-(2-chloro-4-fluoro-phenyl)-imidazo[1,2-a]pyrimidin-3-yl]-(1,1,3,3-tetramethylbutyl)-amine,
(2-anthracen-9-yl-imidazo[1,2-a]pyrazin-3-yl)-tert-butyl-amine,
tert-butyl-(2-naphthalen-1-yl-imidazo[1,2-a]pyridin-3-yl)-amine,
N-cyclohexyl-N-[2-(4,5-dimethyl-furan-2-yl)-imidazo[1,2-a]pyrimidin-3-yl]-acetamide, and
(1,1,3,3-tetramethylbutyl)-[2-(3,4,5-trimethoxy-phenyl)-imidazo[1,2-a]pyridin-3-yl]-amine.

6. A method of alleviating pain in a patient in need thereof, comprising administering to said patient an effective pain alleviating amount of at least one compound of formula I:

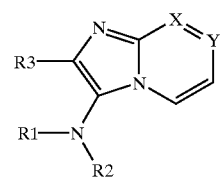

wherein
X and Y each separately denote CH or N, with the proviso that X and Y do not simultaneously denote N;
$R^1$ denotes tert-butyl, $(CH_2)_nCN$, where n=4, 5 or 6, optionally substituted phenyl, $C_4$–$C_8$-cycloalkyl, $CH_2CH_2R$ (R=4-morpholino), 1,1,3,3-tetramethylbutyl, or $CH_2R^a$ wherein $R^a$ represents hydrogen, OH, branched or unbranched $C_1$–$C_8$-alkyl, optionally substituted phenyl, $CO(OR')$ wherein R'=unbranched $C_1$–$C_4$-alkyl or branched $C_1$–$C_5$-alkyl, $PO(OR')_2$ wherein R'=unbranched $C_1$–$C_4$-alkyl or branched $C_1$–$C_5$-alkyl, or $Si(R^xR^yR^z)$ wherein $R^x$, $R^y$ and $R^z$ are each selected independently of one another from branched or unbranched $C_1$–$C_4$-alkyl, $C_4$–$C_8$-cycloalkyl, and phenyl;
$R^2$ denotes hydrogen, $COR^b$, wherein $R^b$ represents branched or unbranched $C_1$–$C_4$-alkyl or $C_3$–$C_8$-cycloalkyl, $CH_2CH_2CO(OR^c)$, wherein $R^c$ represents branched or unbranched $C_1$–$C_4$-alkyl, adamantyl, optionally substituted phenyl, optionally substituted 1-naphthyl, optionally substituted 2-naphthyl, optionally substituted 2-pyridyl, optionally substituted 3-pyridyl, optionally substituted 4-pyridyl, optionally substituted thiazolyl, optionally substituted furoyl, benzyl, $CH_2CH_2R^d$ wherein $R^d$ represents optionally substituted phenyl, or $CONHR^e$ wherein $R^e$ represents branched or unbranched $C_1$–$C_8$-alkyl, $C_3$–$C_8$-cycloalkyl, or optionally substituted phenyl;
$R^3$ denotes methyl, ethyl, tert-butyl, $C_3$–$C_8$-cycloalkyl, phenyl wherein said phenyl is optionally monosubstituted in the 3-, 5- or 6-position, or wherein said phenyl is optionally at least di-substituted in the 4-position and additionally in at least one of the 2-, 3-, 5-, and 6-positions, phenoxy, optionally substituted naphthyl, optionally substituted pyrrole, optionally substituted pyridyl, optionally substituted furan, optionally substituted thiophene, optionally substituted anthracene, optionally substituted phenanthrene, or optionally substituted quinoline;
wherein any radical denoted optionally substituted is unsubstituted, or is at least mono-substituted with a moiety selected from the group consisting of OH, nitro, amino, amido, cyano, CO—$C_1$–$C_8$-alkyl, CO—O—$C_1$–$C_8$-alkyl, $CO_2H$, O—$C_1$–$C_8$-alkyl, O-heteroalkyl, halogen, branched or unbranched $C_1$–$C_8$-alkyl, $C_3$–$C_8$-cycloalkyl, $C_3$–$C_8$-heterocyclyl, unsubstituted or substituted phenyl, unsubstituted or substituted heteroaryl, wherein any ring, aromatic or unsaturated, may be fused to other rings, any moeity optionally has one or more double or triple bonds, and any alkyl or aromatic moiety is unsubstituted or is substituted with a moiety selected from this group;

with the proviso that if $R^1$ is tert-butyl, n-propyl, n-butyl, 1,1,3,3-tetramethylbutyl, cyclohexyl, $CH_2CH_2R$ wherein R=4-morpholino, monosubstituted phenyl, 2,6-dimethylphenyl or benzyl, and $R^2$ is hydrogen or CO(methyl), $R^3$ is not n-propyl, cyclohexyl, unsubstituted phenyl, or phenyl monosubstituted in the 3-position with a carboxylic acid amide group;

with the further proviso that if $R^1$ denotes benzyl, and $R^3$ is methyl, $R_2$ is not hydrogen;

with the further proviso that if $R^1$ is $CH_2C(O)$tert-butyl, and $R^3$ is unsubstituted phenyl, $R^2$ is not hydrogen;

or a pharmaceutically acceptable salt thereof.

7. The method of claim 6, wherein said at least one compound is administered in combination with at least one auxiliary substance.

8. The method of claim 6, wherein $R^2$ denotes hydrogen;

$R^1$ is selected from the group consisting of $(CH_2)_{11}CN$, where n=4, 5 or 6, cyclohexyl, $CH_2CO(O$-methyl), 2,6-dimethylphenyl, 1,1,3,3-tetramethylbutyl, tert-butyl, and n-butyl; and $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)phenyl.

9. The method of claim 6, wherein said at least one compound is selected from the group consisting of (6-isocyano-hexyl)-(2-pyridin-2-yl-imidazo[1,2-a]pyridin-3-yl)-amine, (2-furan-2-yl-imidazo[1,2-a]pyridin-3-yl)-(6-isocyano-hexyl)-amine, (2-cyclohexyl-imidazo[1,2-a]pyrazin-3-yl)-(6-isocyano-hexyl)-amine, (2,6-dimethyl-phenyl)-(2-furan-2-yl-imidazo[1,2-a]pyridin-3-yl)-amine, (2-furan-2-yl-imidazo[1,2-a]pyrazin-3-ylamino)-acetic acid methyl ester, (2-cyclohexyl-imidazo[1,2-a]pyrimidin-3-ylamino)-acetic acid methyl ester, (2-methyl-imidazo[1,2-a]pyrazin-3-ylamino)-acetic acid methyl ester, (2-pyridin-4-yl-imidazo[1,2-a]pyrazin-3-yl)-(1,1,3,3-tetramethyl-butyl)-amine, (2-methyl-imidazo[1,2-a]pyrazin-3-yl)-(1,1,3,3-tetramethyl-butyl)-amine, 3-(3-tert-butylamino-imidazo[1,2-a]pyridin-2-yl)-phenol, butyl-[2-(2,3-dichloro-phenyl)-imidazo[1,2-a]pyrazin-3-yl]-amine,

[(2-phenyl-imidazo[1,2-a]pyridin-3-ylamino)-methyl]-phosphonic acid diethyl ester, tert-butyl-(2-tert-butyl-imidazo[1,2-a]pyridin-3-yl)-amine, butyl-(2-o-tolyl-imidazo[1,2-a]pyrimidin-3-yl)-amine, (2,6-dimethyl-phenyl)-[2-(2-methoxy-phenyl)-imidazo[1,2-a]pyrazin-3-yl]-amine, butyl-(2-o-tolyl-imidazo[1,2-a]pyrimidin-3-yl)-amine, tert-butyl-(2-pyridin-3-yl-imidazo[1,2-a]pyrimidin-3-yl)-amine, tert-butyl-(2-methyl-imidazo[1,2-a]pyridin-3-yl)-amine,

[2-(1H-pyrrol-2-yl)-imidazo[1,2-a]pyrimidin-3-yl]-(1,1,3,3-tetramethyl-butyl)-amine, cyclohexyl-(2-furan-2-yl-imidazo[1,2-a]pyridin-3-yl)-amine, tert-butyl-(2-pyridin-3-yl-imidazo[1,2-a]pyridin-3-yl)-amine, tert-butyl-(2-pyridin-2-yl-imidazo[1,2-a]pyridin-3-yl)-amine, tert-butyl-(2-thiophen-2-yl-imidazo[1,2-a]pyridin-3-yl)-amine, cyclohexyl-(2-methyl-imidazo[1,2-a]pyridin-3-yl)-amine, N-cyclohexyl-N-[2-(5-methyl-furan-2-yl)-imidazo[1,2-a]pyridin-3-yl]-acetamide, tert-butyl-[2-(5-methylsulfanyl-thiophen-2-yl)-imidazo[1,2-a]pyrimidin-3-yl]-amine,

[2-(3-bromo-thiophen-2-yl)-imidazo[1,2-a]pyridin-3-yl]-cyclohexyl-amine, acetic acid 2-methoxy-4-[3-(1,1,3,3-tetramethyl-butylamino)-imidazo[1,2-a]pyrimidin-2-yl]-phenyl ester,

[2-(2-chloro-4-fluoro-phenyl)-imidazo[1,2-a]pyrimidin-3-yl]-(1,1,3,3-tetramethylbutyl)-amine, (2-anthracen-9-yl-imidazo[1,2-a]pyrazin-3-yl)-tert-butyl-amine, tert-butyl-(2-naphthalen-1-yl-imidazo[1,2-a]pyridin-3-yl)-amine, N-cyclohexyl-N-[2-(4,5-dimethyl-furan-2-yl)-imidazo[1,2-a]pyrimidin-3-yl]-acetamide, and (1,1,3,3-tetramethylbutyl)-[2-(3,4,5-trimethoxy-phenyl)-imidazo[1,2-a]pyridin-3-yl]-amine.

10. A process for preparing a compound according to claim 1, comprising selecting amidine, aldehyde, and isonitrile as starting materials;

solvating said starting materials in methylene chloride as a solvent;

adding said starting materials to a reaction vessel successively in sequence (a) amidine, (b) aldehyde, and (c) isonitrile;

forming a three-component reaction thereby; and adding perchloric acid to at least one of said starting materials or reaction vessel.

11. A process according to claim 10, further comprising reacting products formed in said three component reaction with $R^2$Hal or with $R^e$NCO, wherein Hal represents bromine, iodine, or chlorine, and wherein $R^e$ and $R^2$ and are as previously defined.

12. A process according to claim 11, wherein Hal is chlorine.

* * * * *